US009744121B2

(12) United States Patent
Rao et al.

(10) Patent No.: US 9,744,121 B2
(45) Date of Patent: *Aug. 29, 2017

(54) PERSONAL CARE COMPOSITION CONTAINING YEAST/POLYPHENOL FERMENT EXTRACT

(71) Applicant: ARCH PERSONAL CARE PRODUCTS, L.P., South Plainfield, NJ (US)

(72) Inventors: Smitha Rao, Hillsborough, NJ (US); James Vincent Gruber, Washington, NJ (US); Geoffrey Jamison Brooks, Reno, NV (US)

(73) Assignee: ARCH PERSONAL CARE PRODUCTS, L.P., South Plainfield, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/166,669

(22) Filed: May 27, 2016

(65) Prior Publication Data

US 2016/0317433 A1 Nov. 3, 2016

Related U.S. Application Data

(63) Continuation of application No. 12/460,725, filed on Jul. 23, 2009, now Pat. No. 9,376,639.

(60) Provisional application No. 61/135,992, filed on Jul. 24, 2008.

(51) Int. Cl.
| | |
|---|---|
| A61K 36/00 | (2006.01) |
| A61K 8/99 | (2017.01) |
| A61K 8/06 | (2006.01) |
| A61K 36/06 | (2006.01) |
| A61Q 19/00 | (2006.01) |
| C12N 1/16 | (2006.01) |
| A61K 8/11 | (2006.01) |
| A61K 8/14 | (2006.01) |
| A61K 8/34 | (2006.01) |
| C12P 7/22 | (2006.01) |

(52) U.S. Cl.
CPC .............. *A61K 8/99* (2013.01); *A61K 8/06* (2013.01); *A61K 8/11* (2013.01); *A61K 8/14* (2013.01); *A61K 8/347* (2013.01); *A61K 36/06* (2013.01); *A61Q 19/00* (2013.01); *C12N 1/16* (2013.01); *C12P 7/22* (2013.01); *A61K 2800/42* (2013.01); *A61K 2800/48* (2013.01); *A61K 2800/52* (2013.01)

(58) Field of Classification Search
None
See application file for complete search history.

(56) References Cited

U.S. PATENT DOCUMENTS

| | | | |
|---|---|---|---|
| 4,540,571 A | | 9/1985 | Schimanski |
| 5,753,487 A | | 5/1998 | Eigtved et al. |
| 5,866,382 A | | 2/1999 | Hallborn et al. |
| 5,919,684 A | | 7/1999 | Little et al. |
| 6,124,126 A | | 9/2000 | Ito et al. |
| 6,572,882 B1 | | 6/2003 | Vercauteren et al. |
| 7,217,417 B2 | | 5/2007 | Knapp et al. |
| 2005/0158376 A1* | | 7/2005 | Sardi ............... A61K 9/4833 424/451 |
| 2005/0227355 A1 | | 10/2005 | Kjell |
| 2006/0110815 A1 | | 5/2006 | Gruber |
| 2007/0031518 A1 | | 2/2007 | Randolph et al. |

FOREIGN PATENT DOCUMENTS

| | | | | |
|---|---|---|---|---|
| DE | 4027350 A1 | * | 3/1992 | ............... A23F 3/14 |
| HU | 2001004443 A2 | * | 8/2003 | |
| JP | 52120154 | | 10/1977 | |
| JP | 52120154 A | * | 10/1977 | |
| JP | 2008115098 A | | 5/2008 | |
| KR | 2001081839 | | 2/2000 | |
| WO | 03/068161 | | 8/2003 | |

OTHER PUBLICATIONS

Maraz, From yeast genetics to biotechnology. Acta microbiologica et immunologica Hungarica, (2002) vol. 49, No. 4, pp. 483-491.*
Sturm et al, Influence of grape treatment on the wine yeast populations isolated from spontaneous fermentations. Journal of Applied Microbiology (2006), 101(6), 1241-1248.*
Perrot et al., "Yeast adapted to wine: Nitrogen compounds released during induced autolysis in a model wine," J. Indust. Microbial. Biotech., 2002, 29, pp. 134-139.
Arias et al. Yeast Species Associated With Orange Juice: Evaluation of Different Identification Methods; Appl. Environ. Microbiol. Apr. 2002, vol. 68, No. 4, pp. 1955-1961.
Manach et al. Polyphenols; Food Sources and Bioavailability; American Society for Clinical Nutrition; May 2004, vol. 79, No. 5, pp. 727-747.
O'Connor the Claim; Grape Juice Has the Same Benefits as Red Wine: The New York Times, Online, URL< http://www.nytimes.com/2008/09/23/health/23real.html?_r=0 > Sep. 22, 2008,, 2 pages.
Perez-Mendoza et al. Oxoester Oxidoreductase Activities in New Isolates of Pichia anomala From Apple, Grape and Cane Juices; FEMS Yeast Research 5 (2005) pp. 685-690.
Sturm et al. The Cost of Virulence; Retarded Gwoth of *Salmonella typhimurium* Cells Expressing Type III Secretion System 1; Plos Pathogens, Jul. 2011, vol. 7, Issue 7, pp. 1-10.
Masih et al. Characterization of the Yeast *Pichia membranifaciens* and Its Possible Use in the Biological Control of Botrytis cinera, Causing the Grey Mould Disease of Grapevine; FEMS Microbiology Letters 202 (2001) 227-232.

(Continued)

*Primary Examiner* — Qiuwen Mi
(74) *Attorney, Agent, or Firm* — McBee Moore Woodward & Vanik IP, LLC

(57) ABSTRACT

A method of producing yeast-polyphenol ferment extract includes growing the cells of a yeast of *pichia* genus in a growth media to late-logarithmic growth phase, in which the carbon source in the media is exhausted; exposing the cells to a non-cytotoxic dose of polyphenol; and extracting cytoplasmic and extra-cellular components of the exposed yeast cells from the growth media.

11 Claims, 7 Drawing Sheets

(56) References Cited

OTHER PUBLICATIONS

Talron Biotech LTD, Online,URL<http://www.talron.co.il/indexphpmodule=pagemaster&PAGE_user_op=view_page&PAGE_id=250&MMN_position=550:530, accessed Nov. 17, 2011, pp. 1-3.

Howitz et al. "Small molecule activators of sirtuins exend *Saccharomyces cerevisiae* lifespan", Nature, 2003, vol. 425; pp. 191-196.

Borra T.M. et al. "Mechanism of Human SIR TI Activation by Resveratrol"; J. Biol Chem. 280, (2005) 17187.

Ciolino H.P. et al. "Inhibition of Ary! HydrocarborrInduced Cytochrome P-450 IaI Enzyme Activity and CYPIAI Expression by Resveratrol", Mo! Pharm 56 (1999) 4, 760.

Pinto M.D., et al. "Reservatrol is a Potent Inhibitor of the Dioxygenase Activity ofLipoxygenase", J. Agric Food Chem. 47(12), 4842-4846 (1999).

Svobodova A, Jitka Psotova, Daniela Walterova, "Natural phenolics in the prevention of UV-Induced skin damage", Biomed. Papers 147(2), 137-145 (2003).

\* cited by examiner

Control – 1.0 mg total protein

Treatment – 4.7mg/ml total protein

Top = control (Untreated Yeast/Ferment Extract); and
Bottom = Treatment (Yeast/Resveratrol Ferment Extract).

PERSONAL CARE COMPOSITION CONTAINING YEAST/POLYPHENOL FERMENT EXTRACT

CROSS REFERENCES TO RELATED APPLICATIONS

This is a continuation application of application Ser. No. 12/460,725, filed on Jul. 23, 2009, which claims the priorities and benefits of U.S. Provisional Patent Application Ser. No. 61/135,992, filed on Jul. 24, 2008, the disclosures of which are incorporated herein by reference in their entireties.

FIELD OF THE INVENTION

The present invention relates generally to personal care compositions, and methods of making the same. More specifically, the invention relates to personal care compositions containing a yeast-polyphenol ferment extract.

BACKGROUND OF THE INVENTION

Recently, the use of yeast and its derivatives has become very popular in cosmetic applications. This is driven by the fact that yeast, being eukaryotic, has similar cellular biological processes to human cells and is known to trigger the production of beneficial proteins under stress. There is also considerable historical evidence for the use of yeast derivatives and their benefits in topical skin applications by the increase in oxygen uptake. For example, U.S. Pat. No. 4,540,571 discloses yeast derivatives that improve cutaneous respiration. Yeast cell derivatives are also reported to stimulate the production of collagen and elastin in skin cells.

Recent studies suggest that yeast cell extracts have the ability to promote 'growth factors' that stimulates wound healing. For example, U.S. Pat. No. 7,217,417 discloses a method that incorporates yeast cell derivatives into a gel-based formulation for wound healing.

For topical applications, the most commonly used yeast is *Saccharomyces cerevisiae*, also known as baker's yeast. *Saccharomyces* is categorized by the FDA as a "Generally Recognized as Safe (GRAS)" micro-organism. However, products containing *Saccharomyces cerevisiae* or its derivates normally have strong color and characteristic odor. Therefore, there is a need in the cosmetic industry for yeast and yeast extracts that provide beneficial effects to skin's, as well as desirable aesthetic values at the same time.

Resveratrol (3, 4, 5-transhydroxystilbene), a polyphenol found in several plants, has been of considerable interest due to its possible health benefits for treatment of cardiovascular disease, diabetes and cancer. Resveratrol is well known for its presence in red wine and can be extracted from grape skin. Resveratrol can also be found in good abundance in the leaves of various plants such as, for example, Japanese Knotweed (*Polygonum cuspidatum*). Resveratrol is considered to be related to a family of biologically active molecules isolated from plants that are routinely called or referred to as polyphenols. Polyphenols are a group of chemical substances found in plants, characterized by the presence of more than one phenol unit or building block per molecule. Polyphenols include, for example, flavonoids or isoflavonoids, catechins, anthrocyanins and proanthrocyanins.

Several studies in wide range of species have demonstrated the ability of resveratrol to positively affect cellular function and longevity. It is suggested that resveratrol affects cellular longevity by mimicking caloric restriction without requiring any reduction in calorie intake. This is accomplished by the activation of specific proteins, mainly belonging to the "Sirtuins" family of proteins as disclosed by Borra T. M. et. al. in J. Biol Chem. 280, (2005) 17187.

In addition to caloric restriction, resveratrol is also being evaluated for its potential health benefits including triggering DNA-repair mechanisms, anti-carcinogenic and anti-oxidant properties.

Ciolino H. P. et al. discloses that resveratrol may be used to reverse the aging process due to cellular DNA damage. Mol Pharm 56 (1999) 4, 760. In addition, resveratrol has been found to inhibit the activity of several inflammatory enzymes in vitro, including cyclooxygenases and lipoxygenases. Pinto M. D., et al. "Resveratrol is a potent inhibitor of the dioxygenase activity of lipoxygenase." J Agic Food Chem. 47(12), 4842-4846 (1999).

Resveratrol has demonstrated advantages in topical and oral applications, but it suffers from inherent chemical instability and has been shown to be somewhat cytotoxic to skin cells in its native form. It is also quite water-insoluble which makes formulating skin and hair care products with the molecule difficult. A need remains to develop novel ingredients based on resveratrol that are more beneficial and less difficult to work with. As such, it is appreciated that there is a need for an ingredient that provides combined advantages effects of resveratrol and the metabolic pathways of yeast, for use in personal care compositions.

SUMMARY OF THE INVENTION

One aspect of the invention relates to a yeast-polyphenol ferment extract produced by a method comprising the steps of: growing the cells of a yeast of *Pichia* genus in a media to late-logarithmic growth phase wherein the carbon source in the media is exhausted; exposing the cells to a non-cytotoxic dose of polyphenol as a growth factor to generate new active ingredients through metabolic pathways of the yeast; and separating the new active ingredients by filtration or lysing to provide the yeast-polyphenol ferment extract containing the new actives. In a preferred embodiment, the polyphenol is resveratrol dispersed in an organic solvent at a concentration of from about 0.001 gram/liter to 1.0 gram/liter; and the yeast is *Pichia pastoris*.

Another aspect of the invention relates to a personal care composition comprising a yeast-polyphenol ferment extract and a preservative, wherein the preservative is selected from the group consisting of acids, alcohols, glycols, parabens, quaternary-nitrogen containing compounds, isothiazolinones, aldehyde-releasing compounds, halogenated compounds and combinations thereof. The yeast-polyphenol ferment extract is present in a concentration between 0.0001% and 95%, preferably 0.01%-50%, most preferably 0.01%-10% by weight based on the total weight of the personal care composition. The preservative is present in a concentration between 0.01%-10% by weight based on the total weight of the personal care composition. The personal care composition may further comprise a cosmetically acceptable vehicle, and other active ingredients.

A further aspect of the present invention relates to a method of preparing a personal care composition including providing an effective amount of yeast-polyphenol ferment extract and incorporate the extract into a personal care composition.

DETAILED DESCRIPTION OF THE PREFERRED EMBODIMENTS

Figure 1:
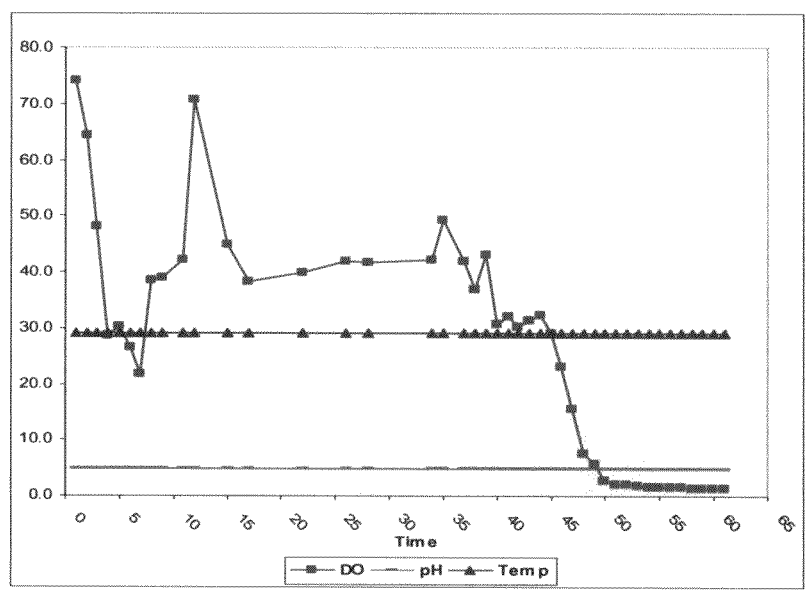
FIG. 1 is a graph depicting the changes of fermentation parameters over time during a yeast/resveratrol fermentation process.

The 'yeast/polyphenol ferment extract' of the present invention is obtained through a specialized process called fermentation. Fermentation occurs when living eukaryotic and/or prokaryotic microorganisms are grown on a nutrient media either in the presence of oxygen (known as aerobic fermentation) or the absence or diminishment of oxygen (known as anaerobic fermentation). The fermentation process can take place with one microorganism, or simultaneously or sequentially with two or more microorganisms (often referred to as co-ferments). The nutrient media is typically a well-defined mixture of proteins, sugars, minerals and the like. Such media is known to a person skilled in the art and may be available through a variety of commercial sources.

The process of metabolizing yeast can occur with a variety of microorganisms such as, for example, yeast, bacillus, molds, plant cells and the like. Especially preferred for the composition of the present invention are ferments made using yeast. As used herein, the term "yeast" is meant to encompass a single yeast cell, multiple yeast cells and/or a culture of yeast cells. The yeast of the present invention can be of various fungal families, known to those skilled in the art including, but not limited to: *Neurospora, Ceratostomella, Claviceps, Xylaria, Rosellinia, Helotium, Sclerotinia, Tulostoma, Rhizopogon, Truncocolumella, Mucor, Rhizopus, Entomophthora, Dictostylium, Blastocladia, Synchytrium, Saprolegnia, Peronospora, Albugo, Pythium, Phytophthora, Plasmodiophora, Tuber, Hydnum, Lecanora, Roccella, Pertusaria, Usnea, Evernia, Ramalina, Alectoria, Cladonia, Parmelia, Cetraria, Agaricus, Cantharellus, Omphalotus, Coprinus, Lactarius, Marasmius, Pleurotus, Pholiota, Russula, Lactarius, Stropharia, Entoloma, Lepiotaceae, Corticium, Pellicularia, Tricholoma, Volvaria, Clitocybe, Flarnmulina, Saccharomyces, Schizosaccharomyces, Saccharomycetaceae, Eurotium, Aspergillus, Thielavia, Peziza, Plectania, Morchella, Wynnea, Helvella, Gyromitra, Phallales, Dictyophera, Mutinus, Clathrus, Pseudocolus, Lycoperdon, Calvatia, Geastrum, Radiigera, Astreus, Nidularia, Gastrocybe, Macowanites, Gastroboletus, Albatrellus, Neolentinus, Nigroporus, Oligoporus, Polyporus, Fistulina, Fomes, Boletus, Fuscoboletinus, Leccinum, Phylloporus, Suillus, Strobilomyces, Boletellus, Tremella, Auricularia, Dacrymyces, Melampsora, Cronartium, Puccinia, Gymnosporangium, Tilletia, Urocystis, Septobasidium, Hygrocybe, Hygrophorus, Hygrotrama, Neohygrophorus, Cortinarius, Gymnopilus, Trichophyton, Microsporum, Monilia, Candida, Cercosporella, Penicillium, Blastomyces, Cercospora, Ustilaginoidea, Tubercularia, Fusarium, Rhizoctinia, Ozonium, Sclerotium, Geoglossum,* or *Armillaria*. Of particular interest are the fungi belonging to the family Saccharomycetaceae. Of greater interest are the fungi belonging to the genus *Pichia*. Of most interest are the fungi belonging to the species *pastoris*. In a preferred embodiment, *Pichia pastoris* is used in the fermentation process.

Typically, yeasts belonging to the phylum *Ascomycetes* are facultative anaerobes; that is they can grow both in the presence or absence of oxygen. For the purpose of the present invention, yeast was aerobically grown and therefore air is critical for growth.

Polyphenols are significant components found in plants and fruits that are responsible for a variety of well known benefits for skin (Svobodová A , Jitka Psotová, Daniela Walterová. Natural phenolics in the prevention of UV-Induced skin damage. Biomed. Papers 147(2), 137-145 2003). Generally polyphenols are extracted from plants. For purposes of this invention, polyphenols can also be prepared by synthetic means. Preferably, the polyphenols suitable for use in the fermentation process of the present invention has a purity of greater than 50%, more preferably, greater than 70% and most preferably, greater than 80%.

It has been surprisingly found that when a yeast belonging to the genus of *Pichia*, for example, *Pichia pastoris*, is exposed to a non-cytotoxic amount of a polyphenol, for example, resveratrol, as a growth factor during a key stage of fermentation, the yeast changes its metabolic pathways and produces new actives that are beneficial to the skin. The produced new actives are relatively stable and do not undergo rapid conversions into less-desired metabolites. Meanwhile, the new actives also have desirable color and odor thus making them an improved ingredient for personal care compositions.

The yeast/polyphenol extracts of the present invention include cytoplasmic and extra-cellular components of the yeast which include, but are not limited to, the nutrient broth, cellular protein material, cellular nucleic material, cellular protoplasmic material and/or cell wall components. Typically, the extracts are relatively water soluble, for example, equal or more than 1-gram of yeast extracts dissolve in 1-gram of water. The extracts may also be soluble in water/organic solvent mixtures such as, but not limited to, aqueous glycols and aqueous glycerols.

The yeast fermentation process can be carried out in a stirred tank bio-reactor. Examples of such bioreactors might include for example, fermentors available from New Brunswick Scientific, Edison N.J. or Applikon Biotechnology Foster City Calif.

To produce a 'yeast/polyphenol ferment extract' of the present invention, *Pichia pastoris* cell culture can be grown between 25° C. to 32° C. in a growth media. An example of a typical yeast fermentation media can be typically found in the "Handbook of Microbiological Media" published by CRC press. For the purpose of this invention, a specific growth media for fermentation of yeast is used. This growth media is chemically defined media and does not have any animal-derived products. In a preferred embodiment, the sole source of carbon in the media of present invention is from glycerol.

To initiate the polyphenol feeding strategy, a non-cytotoxic dose of polyphenol can be dispersed in an organic solvent that is not toxic to the cells to provide a polyphenol feed batch. As used herein, non-cytotoxic dose is defined as a dose where there is no loss in cell viability. In a preferred embodiment, the concentration of the polyphenol in the organic solvent is at least from 0.001 gram/liter to 1.0 gram/liter.

According to one embodiment of the invention, the polyphenol feed-batch is initiated when the cells are in their late-logarithmic growth phase and the carbon source in the media is exhausted (as confirmed by monitoring carbon source in the bioreactor). For polyphenols that are highly hydrophobic, it is critical to monitor the fermentation process to ensure that these polyphenols do not precipitate in the aqueous growth media.

The 'yeast/polyphenol ferment extract' can be obtained by first separating the bio-mass and then extracting active ingredients from the extra-cellular secretions of the yeast. Alternatively, the yeast cell can be lysed to obtain 'yeast/polyphenol ferment lysate' by processes known to those skilled in the art. Typically, the process involves the rupture of the yeast cell walls by chemical, enzymatic or physical means or by combination of these. The 'yeast/polyphenol ferment extract' may be further purified by chromatography, solvent extraction, centrifugation, decantation, filtration or carbon treatment, or other means known to a person skilled in the field. In one embodiment, the 'yeast/polyphenol ferment extract' is further concentrated by any means known to those, skilled in the art, for example, evaporation, spray-drying, lyophylization, belt or drum drying.

After exposing the yeast, for example, Pichia pastoris, to polyphenol growth factor during a key phase of the fermentation process, the yeast has significant genomic and proteomic changes compared to the yeast that is not subjected to the treatment of the polyphenol. In addition, examination of yeast microarrays indicates that various genes within the fermenting pichia pastoris are either upregulated or down-regulated as a result of treatment with the polyphenol. The terms upregulated and downregulated refer to the influence the polyphenol has on signally genes within the yeast to either be turned-on (upregulated) or turned-off (downregulated). The up and down-regulation of the yeast genes can result in changes in protein expression which allows the yeast to express proteins that would not normally be expressed if the polyphenol were not present.

In addition, the Pichia pastoris may ingest the polyphenol and begin to convert the polyphenol into chemical derivatives such as, for example, sugar or protein derived metabolites of polyphenol. The yeast might do this as a means to begin the process of digesting the polyphenol. In particular, if the yeast chemically attaches a protein to the polyphenol on one of the available hydroxyl groups on polyphenol, such molecules might appear in 2D-gel electrophoresis as new proteins. It is difficult to differentiate these new chemically altered polyphenol molecules from normal metabolic proteins that the yeast typically expresses. However, some techniques such as MALDI-TOF Mass Spectroscopy can be used to identify proteins from 2D-gels. In addition, one can examine protein and sugar metabolites of polyphenol by high performance liquid chromatography (HPLC). Without being bound by theory, it is believed that the secondary metabolites of polyphenol formed by fermentation may play a significant role in the ability of the yeast/polyphenol ferment extract to stimulate human skin in beneficial ways not available to just the yeast or the polyphenol alone.

The effect of the yeast/polyphenol ferment extract to influence human skin can be measured in a number of ways known to those skilled in the art. In particular, the yeast/polyphenol ferment extracts can be screened for their effects on skin by employing analytical techniques such as, for example, human genomic microarrays on specific skin cells such as keratinocytes or fibroblasts, or by protein expression analysis on individual skin cells, tissue models or ex vivo or in vivo skin models. In these testing models, specific genes and or proteins may be up-regulated or down-regulated as a result of the extract treatment. Genes and proteins that are capable of regulating skin conditions are of particular interest in the screening. Of particular interest for the purpose of the present invention are genes and proteins related to inflammation, extracellular matrix expression, melanin regulation, skin moisturization, exfoliation and the like. Of particular interest are proteins related to cyclooxygenase expression, in particular cyclooxygenase-1 and 2 and also extracellular matrix protein expression, in particular, types, I, IV and VI collagen expression. In addition, the influence of the extract on skin melanin expression is also of considerable interest.

The effect of the yeast/polyphenol ferment extract on expression of these and other important cutaneous proteins can be monitored by human genomic microarray analysis and protein expression as well as by non-invasive test methods well-known to those in skilled in the art, including, but not limited to, improved moisturization, wrinkle reduction, reduced pigmentation, improved skin tone and the like. Application of the yeast/polyphenol ferment extract can manifest itself by measured reductions in skin wrinkles, for example, as measured by techniques such as SilFlo silicone modeling, PRIMOS and VISIO photographic systems and the like. In addition, moisturization might be measured using transepidermal water loss (TEWL) or cutometer or corneometric measurements. Likewise, skin pigmentation could be measured using a chromometer. Such testing technologies are well-known to those skilled in the art and can be found in Handbook of non-invasive methods and the skin, $2^{nd}$ edition, Serup J, Jemec GBE, Grove GL (ed.), Taylor and Francis Boca Raton Fla. 2006, the disclosure of which is incorporated herein by reference in its entirety.

Figure 4:
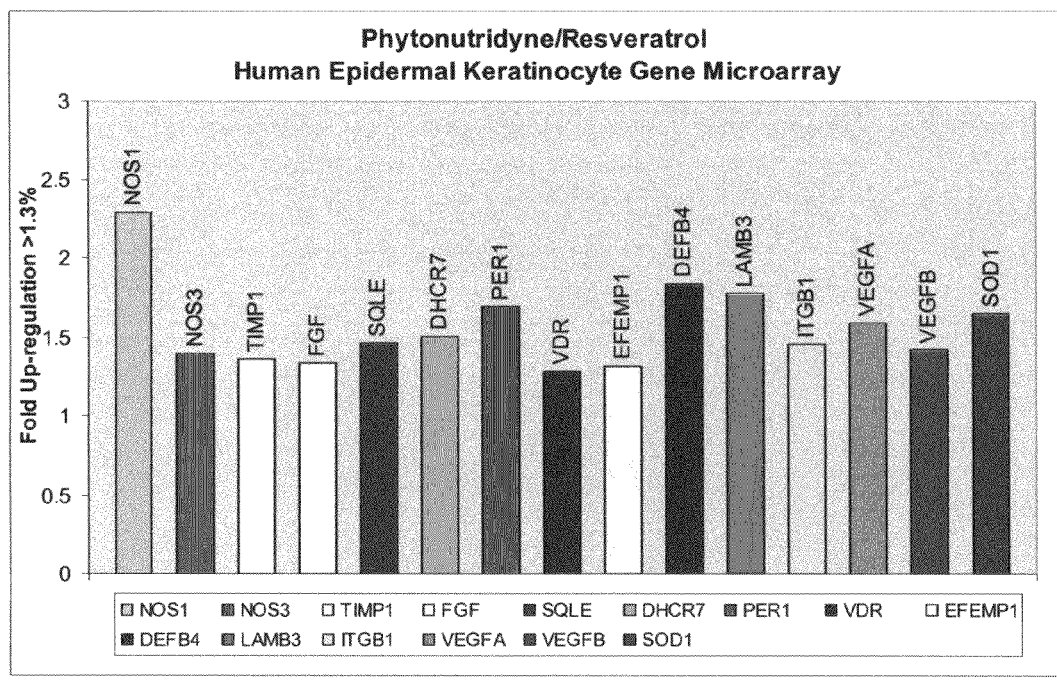
FIG. 4 is a graph of relative expression of genes by the treatment of a yeast/resveratrol ferment extract on human epidermal keratinocytes.

As shown, for example, in FIG. 4, human gene microarray analysis on human epidermal keratinocytes indicates that the yeast-resveratrol ferment extract up-regulates several genes involved in various skin metabolism functions. It is thus appreciated that the yeast-polyphenol ferment extract according to the present invention can be used in personal care compositions.

The personal care composition of the present invention may contain an effective amount of 'yeast/polyphenol ferment extract' and at least one preservative selected from the group consisting of acids, alcohols, glycols, parabens, quaternary-nitrogen containing compounds, isothiazolinones, aldehyde-releasing compounds and halogenated compounds. Illustrative alcohols include phenoxyethanol, isopropyl alcohol, and benzyl alcohol; illustrative glycols include propylene, butylene and pentylene glycols; illustrative parabens include (also known as parahydroxybenzioc acids) methyl, propyl and butyl parabens; illustrative quaternary nitrogen containing compounds include benzalkonium chloride, Quartenium 15; illustrative isothiazoles include methylisothiazoline, methychlorolisothiazoline; illustrative aldehyde releasing agents include DMDM hydantion, imiadolidinyl urea and diazolidinyl urea; illustrative anti-oxidants include butylated hydroxytoluene, tocopherol and illustrative halogenated compounds include triclosan and chlorohexidene digluconate. Examples of preservatives useful for the purpose of the present invention can be found in Steinberg, D. "Frequency of Use of Preservatives 2007". Cosmet. Toilet. 117, 41-44 (2002) and, "Preservative Encyclopedia" Cosmet. Toilet. 117, 80-96 (2002). In addition, enzyme preservative systems such as those described in the article by Ciccognani D. Cosmetic Preservation Using Enzymes. in "Cosmetic and Drug Microbiology", Orth DS ed., Francis & Taylor, Boca Raton, Fla. (2006) can also be effective for use with the composition of the present invention.

The amount of 'yeast/polyphenol ferment extract' present in a personal care composition is between 0.001% and 95% based on the total weight of the personal care composition, preferably between 0.01% and 50%, more preferably between 0.01% and 10%. The preservative is present in a concentration between 0.01% and 10% by weight based on the total weight of the composition.

Additionally the 'yeast/polyphenol ferment extract' can optionally contain other functional ingredients such as, water, surfactants, emulsifiers, conditioners, emollients, waxes, oils, polymers, thickeners, fixatives, colorants, humectants, moisturizers, stabilizers, diluents, solvents and fragrances. In addition the personal care composition may contain active ingredients such as botanicals, nutraceuticals, cosmeceuticals, therapeutics, pharmaceuticals, antifungals, antimicrobials, steroidal hormones, antidandruff agents, anti-acne components, sunscreens, preservatives and the like.

The 'yeast/polyphenol ferment extract' can be used in various types of cosmetic formulations including, but not limited to lotions, ointments, creams, sprays, spritzes, aqueous or aqueous-alcoholic mixture gels, mousses, patches, pads, masks, moistened clothes, wipes, solid sticks, clear sticks, lip sticks, aerosol creams, anhydrous powders, talcs, tonics, oils, emulsions and bath salts. Such cosmetic formulations may be used as a topical application on the skin.

The 'yeast/polyphenol ferment extract' of the present invention many include the extract alone or they may include the 'yeast/polyphenol ferment extract' encapsulated in various chemical delivery vehicles including, but not limited to, liposomes, niosomes, sub-micron emulsions, polymeric encapsulates, gels, creams, lotions, and combinations thereof.

The following examples are intended to illustrate the art of the present invention and are not intended to limit the scope of the claims below.

EXAMPLE—1

Preparation of Yeast/Reveratrol Ferment Extract

Organism and Media

Yeast cell culture was obtained from ATCC (*Pichia pastoris* # 60372). Stock cultures were maintained on yeast-peptone-dextrose (YPD) agar plates. The parent stock culture was grown in YPD broth and maintained at −20° C. The fermentation was carried out in Yeast Nitrogen-Base (YNB) growth media and supplemented with glycerol containing, 2.7% H3PO4, 0.09% $CaSO_4$, 1.8% $K_2SO_4$, 1.5% $MgSO_4$, 0.41% KOH, 4% glycerol (Sigma St. Louis, Mo.). Resveratrol (>98%) was purchased from Wilshire Technologies (Princeton. N.J.). Antifoam sigma-emulsion B was used throughout the process (Sigma, St. Louis, Mo.).

Fermentor

After optimization of treatment via the shake flask trials, the process was scaled up to 2 L and 15 L fermentation stages (2 L New Brunswick Scientific, Edison N.J. and 15 L Applikon Biotechnology Foster City Calif.).

Stress Conditions

Fed-batch cultures were grown at 29° C., in Yeast Nitrogen-Base (YNB) growth media and supplemented with glycerol (2.7% $H_3PO_4$, 0.09% $CaSO_4$, 1.8% $K_2SO_4$, 1.5% $MgSO_4$, 0.41% KOH, 4% glycerol). The pH was kept constant at 5.0±0.5 by titration with 2M $NH_4OH$. The dissolved oxygen levels were measured by a sterilizable DO probe and the oxygen saturation was kept at 30% by regulating the stirring velocity between 100 and 600 rpm. The aeration rate was set at 1 VVM. Resveratrol feed was initiated at the concentration of 0.001 mg/ml. This method was successfully scaled up from bench-top to pilot-scale to production.

An overview of the yeast/resveratrol fed-batch fermentation process is shown in FIG. 1. The pH, temperature and other fermentation parameters were constantly monitored to reflect the batch process. The resveratrol-feed stage focuses on uptake of resveratrol by the microorganism, in a nutrient-limited environment.

For the purpose of further testing, samples collected at 4, 8, 12, 24 hours after resveratrol feed was initiated, indicate that there is no evidence of toxicity of cells as measured by changes in optical density and viable cell counts.

EXAMPLE—2

Effect of Yeast-Resveratrol Fermentation Process on Yeast Protein Expression

2Dimensional Gel Electrophoresis

Figure 2:
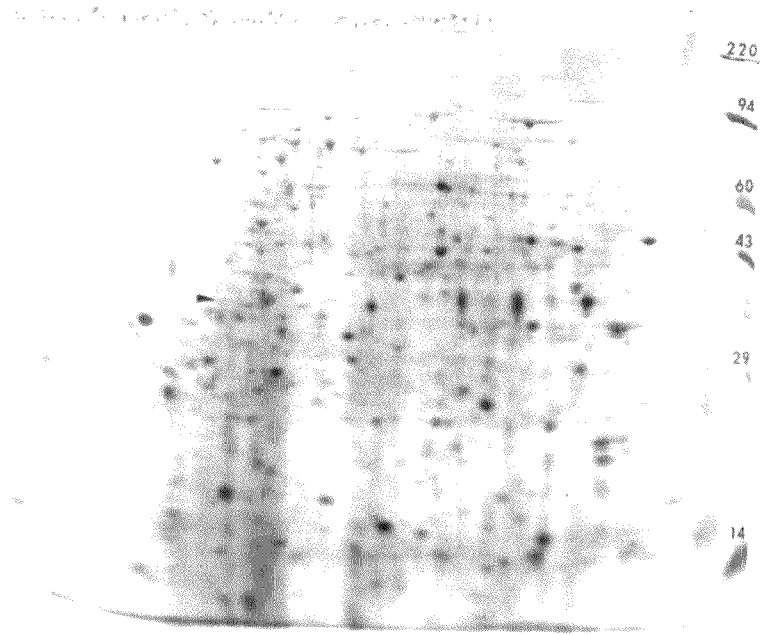
FIG. 2 shows a 2D gel electrophoresis comparison of a non-treated yeast extract (control) and a resveratrol treated yeast extract.
Figure 2:
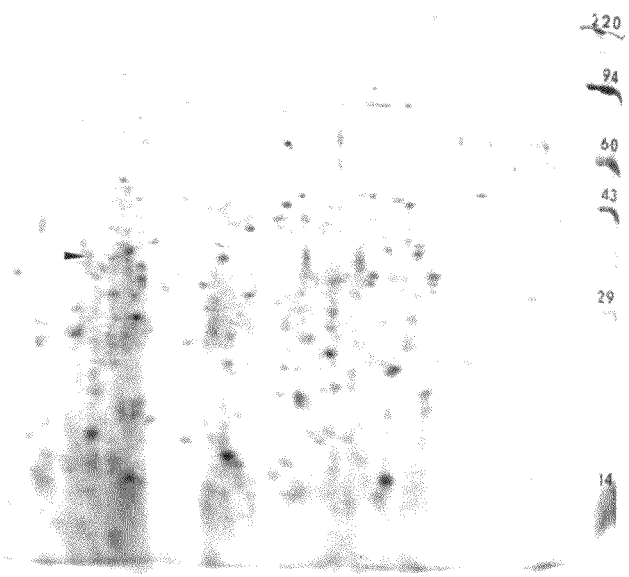

To identify the metabolic changes in the yeast because of the polyphenol feed-strategy, 2-Dimensional gel electrophoreses and gene microarray analysis was conducted on the control, (i.e., a yeast extract without resveratrol growth factor), and a yeast-resveratrol ferment extract produced by the process of the present invention. The first dimension IEF focuses on separation of the proteins based on their isoelectric points and was conducted using the Ettan1PGphor system with a manifold for protein loading. The 2nd dimension SDS-PAGE is an electrophoretic method for separating polypeptides according to their molecular weights using the DALT VI Electrophoresis Unit (GE-Amersham, Piscataway N.J.) (2, 6). To remove interfering substances and impurities, the yeast cell extracts were purified using the 2D Clean-up kit provided by GE Amersham. Each purified yeast sample was rehydrated overnight with Thiourea rehydration solution (7M Urea and 2M Thiourea, 2% Chaps, 0.5% Pharmalyte). The rehydrated samples were loaded onto the $1^{st}$ dimension IEF. Following the $1^{st}$ dimension IEF, the strips were equilibrated and loaded onto the $2^{nd}$ dimension DALT VI. The gels were stained using Coomassie with sensitivity ranging from 10-500 ng protein concentration. Details of the 2Dimentional Gel Electrophoresis method can be found in United States Patent Application Publication No. US2006/0110815 A1, the disclosure of which is incorporated herein by reference in its entirety. The results of 2-Dimensional Gel Electrophoresis for the control, i.e., the untreated yeast ferment extract, and the yeast-resveratrol ferment extract are shown in FIG. 2.

Figure 3:
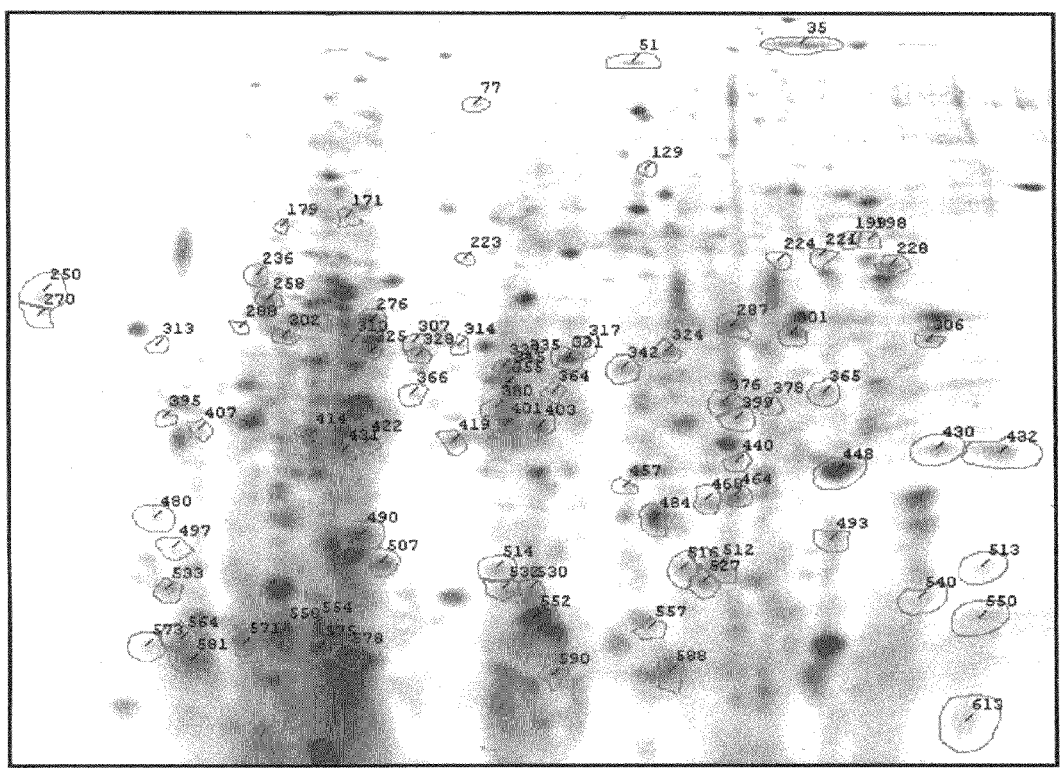
FIG. 3 shows a 2D gel laser densitometer comparison of a non-treated yeast extract (control) and a resveratrol treated yeast extract.

FIG. 3 illustrates the laser densitometer comparison of the control versus the yeast/resveratrol of the invention. Reference spot numbering, pI, and MW are given for changing polypeptide spots and analyzed in the samples. Polypeptide spots that are increased in yeast/resveratrol of the invention versus the control by a fold of >1.7 and have a p value <0.05 are highlighted in blue. A total of 626 spots were analyzed.

The results indicate that after exposing the yeast to resveratrol growth factor during a key phase of the fermentation process, the yeast has significant proteomic changes (i.e., new proteins have either been expressed or older existing proteins are now being suppressed as a result of the resveratrol treatment).

EXAMPLE—3

Gene Microarray Analysis on Human Epidermal Keratinocytes

After treatment with resveratrol in a procedure as illustrated in example 1, the yeast cells were centrifuged and the pellet was re-suspended in RNA Later (Ambion) and stored at 4° C. Total RNA was extracted from the yeast using a RiboPure RNA extraction kit (Ambion), and mRNA was subsequently amplified using a Message AMP aRNA Kit (Ambion). For the array, samples of aRNA were fluorescently labeled with either Cy-3 or Cy-5 using a MicroMax array labeling kit (Perkin Elmer). Labeled aRNA was then applied to a Yeast Genome DNA Microarray chip (Agilent Technologies), and hybridized overnight. On the following day the chips were washed, scanned with an Axon 4100A DNA microarray scanner and analyzed using Axon Genepix-Pro® software. The method employed for gene microarray analysis can be found in United States Patent Application Publication No. US2006/0110815.

The genes of interest obtained from the human epidermal keratinocyte gene-microarray were carefully screened for their potential role in skin functions. The molecular chip generated from human epidermal keratinocytes gene-microarray showed distinctive results in various differentially expressed genes. Genes that were of interest were observed at different time periods of treatment to obtain a time-response for a specific gene. The gene expression was monitored to obtain a time-related response to the resveratrol nutritional strategy. The up-regulation of several genes involved in various skin metabolism functions were detected. As shown in FIG. 4, yeast/resveratrol ferment extract causes statistically significant changes in genes such as NOS1, FER1, DEFB4, LAMB3, COX1, COX2, COL4A1, COL1A1, COL1A2, COL6A1, COL6A2 and SOD1. Numerous other genes such as NOS3, TMMP1, DHCR7 and VEGFA were also up-regulated by the application of yeast/resveratrol ferment extract.

For purpose of gene microarray analysis, the term "up-regulation" or "up-regulated" implies that the gene is over-expressing RNA. The term "down-regulation" or "down-regulated" implies RNA is being under-expressed.

EXAMPLE—4

Full Thickness Evaluation

Figure 5:
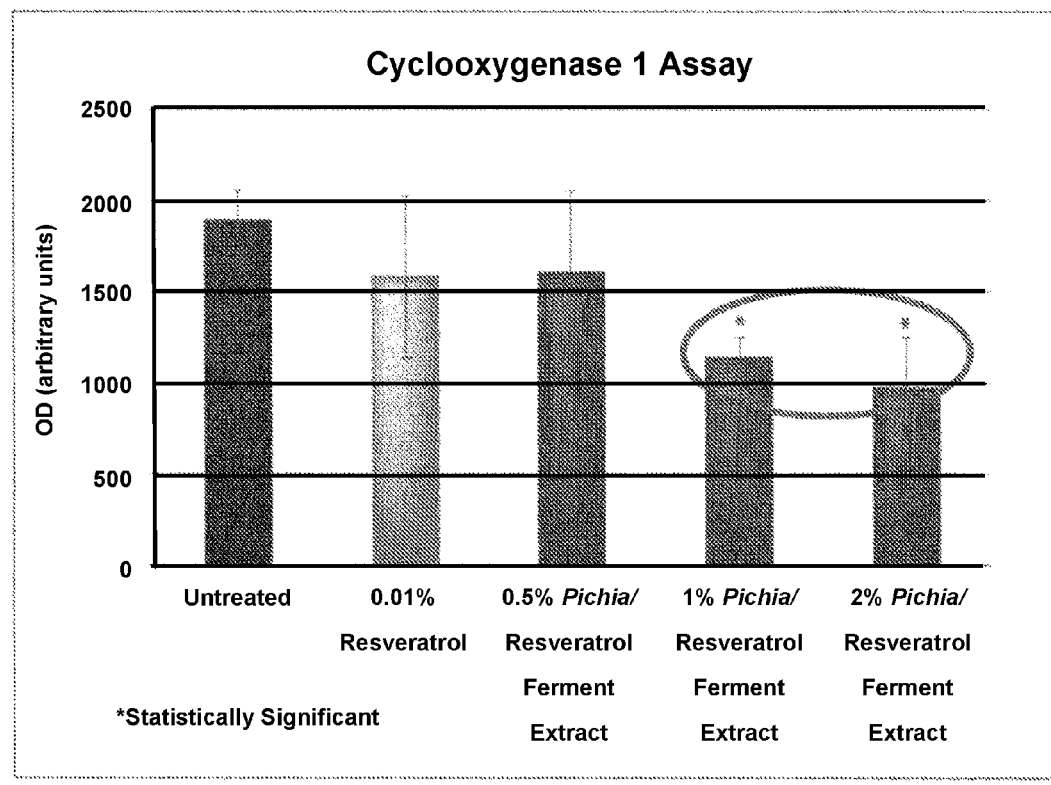
FIG. 5 is a graph illustrating the effect of yeast/resveratrol ferment extracts to COX1 enzyme.
Figure 6:
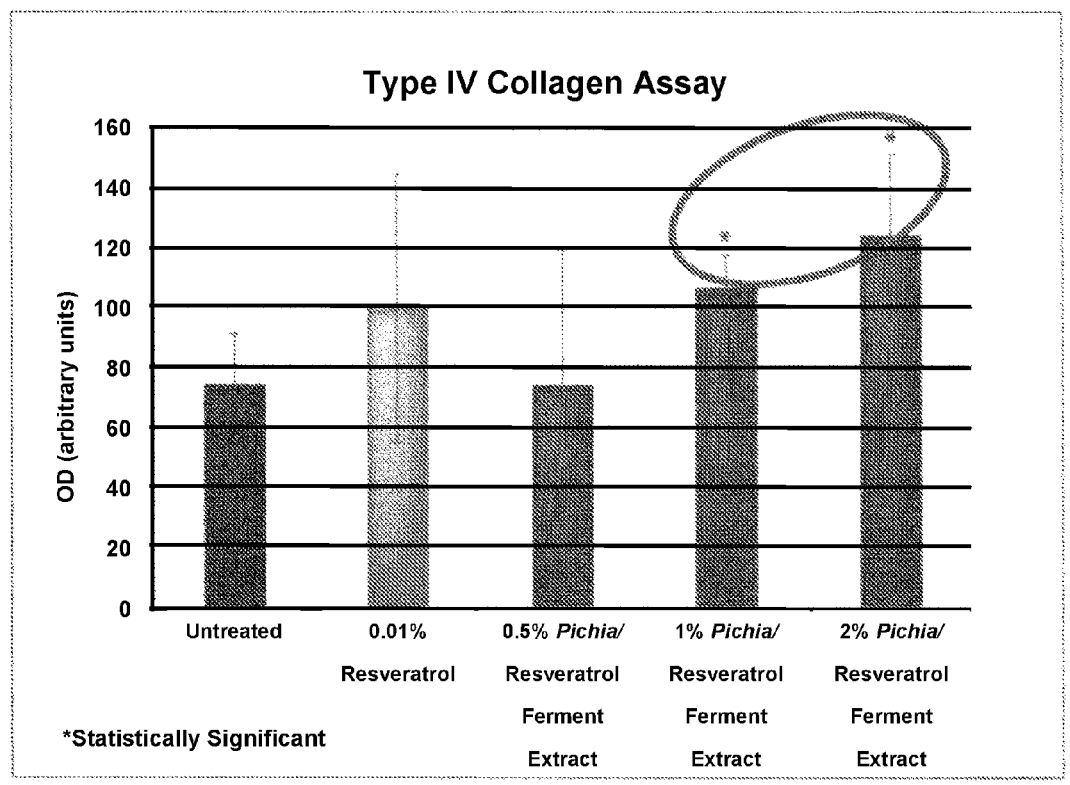
FIG. 6 is a graph illustrating the effect of yeast/resveratrol ferment extracts to Type IV collagen protein.
Figure 7:
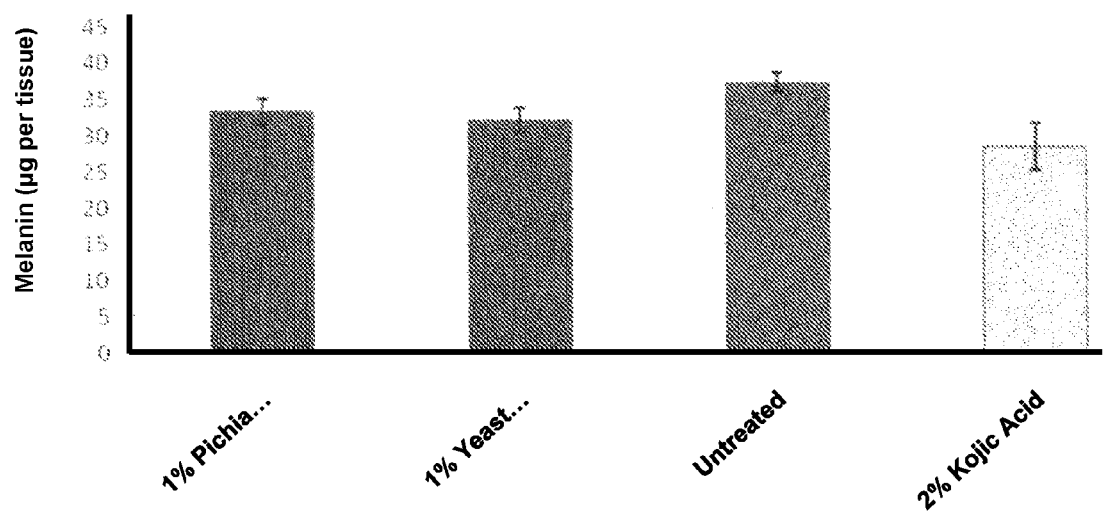
FIG. 7 is a graph illustrating the effect of yeast/resveratrol ferment extracts to the expression of melanin.

The yeast/resveratrol ferment extracts of the invention were tested on the MatTek full thickness skin tissue model. This skin model consists of: 1) normal human-derived epidermal keratinocytes that have been cultured to form a multilayered, highly differentiated model of the human epidermis and, 2) human fibroblasts that have been seeded into a collagen matrix to form the dermis. Upon arrival, the tissues were stored at 4° C. until used. For use, the tissues were removed from the agarose-shipping tray and placed into a 6-well plate containing 4 ml of assay medium and allowed to equilibrate overnight at 37±2° C. and 5±1% CO2. After the overnight equilibration, the media was replaced with 4 ml of fresh media and 50 µl of test material was then applied topically to the tissues. The tissues were then incubated for 24 hours at 37±2° C. and 5±1% CO2.
COX Assay A membrane was equilibrated in Tris Buffered Saline (TBS: 20 mM Tris, pH 7.5, 150 mM NaCl) and assembled into a Bio-Dot microfiltration apparatus. After assembly, 200 µl of TBS was added to each well used in the Bio-Dot and the vacuum was applied to ensure that there was adequate flow through all of the wells. Next, each cell culture media sample (400 µl) or protein homogenate sample (approximately 5 µG) was assigned a well in the apparatus and was applied to the appropriate well. The samples were filtered under low vacuum. TBS was added to wells not assigned a sample to ensure that the membrane did not dry out during the procedure. At the end of the blotting procedure and additional 200 µl was applied and filtered through each well. The membrane was then removed from the Bio-Dot apparatus, washed in TBS for 5-10 minutes and then placed into blocking solution (Tris Buffered Saline [20 mM Tris, pH 7.5, 150 mM NaCl, 1% non-fat milk powder) and allowed to incubate for at least 1 hour at room temperature on a rocking platform. The results of the assay are shown in FIG. 5.
Type IV Collagen Assay A series of type I C-peptide standards was prepared ranging from 0 ng/ml to 500 ng/ml. An ELISA microplate was prepared by removing any unneeded strips from the plate frame. In each well to be used 100 µl of sample or standard was added and the plate was incubated for 1 hour at 37° C. After the incubation, the plate was washed three times with wash buffer. After the last wash was removed, 100 µl of detection solution was added to each well and the plate was incubated for 1 hour at 37° C. After the incubation, the plate was washed again as described above. When the last wash was removed 100 µl of substrate solution was added to each well and the plate was incubated at 37° C. for 30 minutes. After the incubation, 50 µl of stop solution was added to each well and the plate was read at 460 nm using a plate reader. The results of the assay are shown in FIG. 6.
Melanin Assay on SkinEthic Tissue SkinEthic's Tanned Epidermis model consists of normal, human-derived epidermal keratinocytes and melanocytes that have been co-cultured to form a multilayered, highly differentiated model of the human epidermis. The melanocytes within this model undergo melanogenesis, leading to a basal level of melanin accumulation within the tissues over time which can be influenced by test materials that can either increase (skin darkening agents) or decrease (skin whitening agents) melanin synthesis. The results shown in FIG. 7 demonstrates that yeast/resveratrol ferment extract of the invention minimized the expression of melanin.

EXAMPLE—5

Preparation of Liposomal Encapsulated Yeast/Resveratrol Ferment Extract

Samples of 'yeast/resveratrol ferment extract' were incorporated into liposome comprising phospholipid and lecithin layer obtained from soybeans. The lysate was slurried together with liposome using a high-pressure homogenizer obtained from Hydraulic Engineering Corporation (Brea, Calif.). The milky white mixture contained the 'yeast/resveratrol ferment extract' encapsulated with the liposomal components.

EXAMPLE—6

Preparation of Maltodextrin-Encapsulated Yeast/Resveratrol Ferment Extract

Samples of 'yeast/resveratrol ferment extract' were encapsulated in maltodextrin and spray-dried to essentially provide an anhydrous powder of maltodextrin-encapsulated 'yeast/resveratrol ferment extract' using the methodologies in WO2003/068161. The reference is incorporated herein in its entirety.

The following proposed examples illustrate skin care compositions according to the present invention that can be prepared using the 'yeast/resveratrol ferment extract' as prepared using example-1.

PROPOSED EXAMPLE—7

Water-in-Oil Emulsion

The example illustrates a high internal phase water-in-oil emulsion incorporating the 'yeast/resveratrol ferment extract' prepared as disclosed in Example-1.

| Ingredient | Wt % |
|---|---|
| 1,3-dimethyl-2-imidazolidione | 0.2 |
| Polyoxylene (2) oleyl ether1 (Oleth-2) | 5.0 |
| Disteardimonium Hectorite | 0.5 |
| MgSO4•7H2O | 0.3 |
| Preservative[2] | 0.01 |
| Yeast/Resveratrol Ferment extract | 10.0 |
| Water | To 100 |

PROPOSED EXAMPLE—8

Oil-in-Water Cream

The example illustrates an oil-in-water cream incorporating the 'yeast/resveratrol ferment extract' prepared as disclosed in Example-1.

| Ingredient | Wt % |
|---|---|
| Mineral Oil | 4 |
| 1,3-dimethyl-2-imidazolidione | 1 |
| Ceteth-10 | 4 |
| Cetyl Alcohol | 4 |
| Triethanolamine | 0.75 |
| Butylene Glycol | 3 |
| Xanthum Gum | 0.3 |
| Methyl, Propyl, and Butyl Paraben | 0.01 |
| Yeast/Resveratrol Ferment extract | 10.0 |
| Water | To 100 |

PROPOSED EXAMPLE—9

Alcoholic Lotion

The example illustrates an alcoholic lotion incorporating the 'yeast/resveratrol ferment extract' prepared as disclosed in Example-1.

| Ingredient | Wt % |
|---|---|
| 1,3-dimethyl-2-imidazolidione | 0.3 |
| Ethyl Alcohol | 40 |
| Yeast/Resveratrol Ferment Extract | 10.0 |
| Water | To 100 |

PROPOSED EXAMPLE—10

Sub-Micron Emulsion Concentrate

The example illustrates a sub-micron emulsion concentrate that contains the 'yeast/resveratrol ferment extract' prepared as disclosed in Example-1.

| Ingredient | Wt % |
|---|---|
| Trimethylopropane Tricaprylate/Tricaprate | 18.0 |
| Glycerin | 8.0 |
| Cetcaryl alcohol | 2.0 |
| Cetcareth 20 | 2.0 |
| Glyceral stearate | 2.0 |
| Butylated Hydroxytoluene | 0.01 |
| Yeast/Resveratrol Ferment Extract | 10.0 |
| Water | To 100 |

PROPOSED EXAMPLE—11

| Ingredient | Wt % |
|---|---|
| Water | 89 |
| 'yeast/resveratrol ferment extract' | 10.0 |
| Preservative | 1 |

What is claimed is:

1. A method of producing yeast resveratrol ferment extract comprising:
   growing the cells of a yeast of *Pichia* genus in a growth media to late-logarithmic growth phase, wherein the carbon source in said media is exhausted;
   exposing said cells to a non-cytotoxic dose of resveratrol;
   rupturing a yeast cell wall; and
   extracting cytoplasmic and extra-cellular components of the exposed yeast cells from the growth media.

2. The method of claim 1, wherein the yeast is *Pichia pastoris*.

3. The method of claim 1, wherein the media does not include any animal-derived products.

4. The method of claim 1, wherein the resveratrol is dispersed in an organic solvent at a concentration of from about 0.001 gram/liter to 1.0 gram/liter.

5. The method of claim 1, wherein the yeast resveratrol ferment extract comprises cellular components consisting of cellular protein material, cellular nucleic material, cellular cytoplasmic material and cell wall components.

6. The method of claim 1, wherein the extracted cytoplasmic and extra-cellular components of the exposed cells are relatively water-soluble.

7. The method of claim 1, further comprising forming a personal care composition comprising the yeast-resveratrol ferment extract and a preservative,
   wherein the preservative is selected from the group consisting of acids, alcohols, glycols, parabens, quaternary-nitrogen containing compounds, isothiazolinones, aldehyde-releasing compounds, halogenated compounds, and combinations thereof.

8. The method of claim 7, wherein the preservative is present at a concentration between 0.01% and 10% by weight based on the total weight of the personal care composition.

9. The method of claim 7, wherein the yeast-resveratrol ferment extract is encapsulated within a encapsulant to control the release rate of the extract, wherein the encapsulant is selected from the group consisting of liposomes, niosomes, sub-micron emulsions, polymeric encapsulates, gels, creams, lotions, and combinations thereof.

10. The method of claim 7, wherein the personal care composition further comprises a cosmetically acceptable vehicle.

11. The method of claim 7, wherein the personal care composition further comprises at least one ingredient selected from the group consisting of water, surfactants, emulsifiers, conditioners, emollients, waxes, oils, polymers, thickeners, fixatives, colorants, humectants, moisturizers, stabilizers, diluents, solvents, fragrances, botanicals, nutraceuticals, cosmeceuticals, therapeutics, pharmaceuticals, antifungals, antimicrobials, steroidal hormones, antidandruff agents, anti-acne components, sunscreens, preservatives, and combinations thereof.

* * * * *